United States Patent [19]
Stamvik et al.

[11] Patent Number: 4,537,722
[45] Date of Patent: Aug. 27, 1985

[54] STEROID ESTERS PREPARATION

[75] Inventors: Anders R. Stamvik; Sten K. Kristensson, both of Helsingborg; Karl-Erik Lundvall, Ängelholm, all of Sweden

[73] Assignee: Ab Leo, Helsingborg, Sweden

[21] Appl. No.: 614,991

[22] Filed: May 29, 1984

[30] Foreign Application Priority Data

May 30, 1983 [SE] Sweden .............................. 8303031

[51] Int. Cl.$^3$ ............................................. C07J 17/00
[52] U.S. Cl. ............................. 260/397.4; 260/397.45; 260/397.47; 260/397.5
[58] Field of Search ........................ 260/397.4, 397.45

[56] References Cited

U.S. PATENT DOCUMENTS 4,177,269 12/1979 Fex et al. .................... 260/239.5
4,180,504 12/1979 Hansen et al. ............. 260/239.55 D

FOREIGN PATENT DOCUMENTS 1050883 12/1966 United Kingdom ....... 260/239.55 R

Primary Examiner—Elbert L. Roberts
Attorney, Agent, or Firm—Gordon W. Hueschen

[57] ABSTRACT

This invention relates to an improved steroid ester synthesis in which carbodiimides and catalytic amounts of 4-(tertiary amino)-pyridines, in combination with acid catalysts, are used as condensing agents, resulting in pure, non discolored compounds in high yields.

19 Claims, No Drawings

STEROID ESTERS PREPARATION

FIELD OF INVENTION

This invention relates to an improved steroid ester synthesis in which carbodiimides and catalytic amounts of 4-(tertiary amino)-pyridines, in combination with acid catalysts, are used as condensing agents, resulting in pure, non discoloured compounds in high yields.

BACKGROUND OF THE INVENTION

In the following, references to the literature are given by numbers within brackets. The numbers refer to literature sources listed after the examples.

PRIOR ART

The preparation of carboxylic acid esters using a carbodiimide as a reaction partner is, i.a., known from (1) and (2) and these references are discussed as A and B below.

A: From a US-patent (1) a process is known for the preparation of carboxylic acid esters, whereby a carboxylic acid and a hydroxyl compound are reacted in the presence of a carbodiimide, pyridine, or 3- or 4- lower alkylpyridine, and a strong acid. The inventive step in said process is the presence of the strong acid, which improves the yield by decreasing the simultaneous formation of an N-acylurea compound from the carbodiimide and the carboxylic acid. The formation of said by-product is illustrated below:

$R^1{-}COOH + R^2{-}N{=}C{=}N{-}R^3 \longrightarrow$

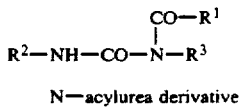

$$R^2{-}NH{-}CO{-}\underset{\underset{CO{-}R^1}{|}}{N}{-}R^3$$

N—acylurea derivative

The preparation of steroid carboxylic acid esters is illustrated in some examples of said patent.

In none of these examples is anything said about the colour of either the reaction mixture or the esters obtained.

We have now found (see Examples Nos. 1-3) that, when the alcohol is a steroid hydroxyl compound having a cyclopentanophenanthrene carboncarbon skeleton, even if the steroid esters obtained have the expected melting points, they are nevertheless discoloured after the recrystallization, and that these discolourations cannot be removed by further recrystallizations even if activated carbon or silica gel is used in such purification procedure. The same esters have a white or at most an off-white colour when prepared in the absence of the strong acid, even though yields are greatly reduced. On the contrary, all experiments using non-steroid alcohols have resulted in colourless reaction mixtures even in the presence of the strong acid. The inventors of the U.S. patent (1) have published a paper, (3), where they describe the preparation of the steroid esters found in their patent examples Nos. 3 and 5. The first ester is said to be cream-coloured and the second one to be pale yellow.

The reasons why said discolourations occur with steroids are not understood. Even if the catalytic amount of the strong acid is reduced to about 0.005 mol of the limiting ester-forming component, the steroid ester obtained is still discoloured.

Experiments, wherein pyridine is used in a catalytic amount together with a cosolvent, give the result that the esterification process is not completed.

From what has been said in the foregoing it is quite clear that preparing steroid esters, using the method described in (1), is of little advantage. True, employment of a catalytic amount of a strong acid results in high yields by suppressing the formation of N-acylureas when pyridine is used as a solvent, but the esters thus obtained are discoloured.

B: The esterification of an acid with an alcohol using dicyclohexylcarbodiimide (in the following abbreviated as DCC) as a condensing agent is activated by adding a catalytic amount of 4-dimethylaminopyridine (in the following abbreviated as DMAP), (2). Under such reaction conditions, the formation of side products is said to be suppressed. Only lower alkanols have been investigated and crystalline products were obtained only after a purification step, using a silica gel column.

We have now repeated the reaction procedure described in said publication in the esterification of various steroid alcohols with various carboxylic acids (see Example No. 4). In all experiments made we found that N-acylurea compounds were formed and, with acids having higher molecular weights, that these by-products are especially difficult to remove by recrystallization. Using the same molar ratio between steroid and acid, unchanged steroid was always found when the reaction was finished, which showed that part of the carboxylic acid used was consumed in forming N-acylureas. When expensive carboxylic acids having higher molecular weights are used, it is a significant disadvantage that these acids are consumed in forming the N-acylureas.

According to the present invention it has now been found that the problems mentioned above can be avoided by using a combination of a strong acid and a pyridine having a tertiary amino group in the 4-position. When using this combination, the formation of N-acylureas is suppressed down to negligible amounts and the steroid esters can be prepared in high yields as pure compounds without any discolourations.

As is seen from the examples Nos. 5-8, steroid hydroxyl compounds which have a cyclopentanophenanthrene carbon-carbon skeleton containing up to a maximum of 40 carbon atoms and having a primary, a secondary, or a phenolic hydroxy group, can be esterified with carboxylic acids to give excellent yields of esters of high purity and colour when approximately equimolar amounts of the reacting carboxylic acid and the steroid hydroxyl compound are employed. The esterification process has to be performed in an inert organic solvent using a carbodiimide as a condensing agent and in the presence of a pyridine, having a tertiary amino group in the 4-position, such as a di-(lower-alkyl)amino-, a pyrrolidino-, a piperidino-, a morpholino-, or a 4-methyl-1-piperidinyl-group, and a strong acid. Even though both the 4-(tertiary amino)-pyridine and the strong acid are preferably used in catalytic amounts, it has been found advantageous to use a molar amount of the strong acid which is less than the molar amount of 4-(tertiary amino)-pyridine employed.

Even if it is known that the addition of a strong acid in the above type of reaction increases the yield of the ester formed when the reaction is performed with pyridine as a solvent, the products obtained in this reaction are always discoloured when the alcohol employed is a steroid having the cyclopentanophenanthrene carbon-carbon skeleton. It is also known that use of a catalytic amount of 4-dimethylaminopyridine as a catalyst in esterification processes, where dicyclohexylcarbodiimide is also employed, gives improved yields in the esterification of certain carboxylic acids with lower alkanols.

In spite of these known facts, it could not be foreseen that adding a catalytic amount of a strong acid to the reaction mixture in the latter case would practically prevent the formation of N-acylureas and discolouring impurities resulting in esters of high purity and colour and in improved yields. This effect is of course especially valuable when such N-acylureas and/or discolouring impurities are difficult to remove from the esters formed.

Steroid alcohols esterified with valuable carboxylic acids are such a type of ester which is preferably synthesized by the method of the present invention. This class of ester is of great pharmaceutical interest, for example as including numerous anti-tumor agents and long-acting hormonal agents.

SUMMARY OF THE INVENTION

The object of the invention is to provide a process for the preparation of a steroid carboxylic acid ester of high purity and in improved yield and colour.

The process comprises reacting, in an inert organic solvent, which is nonreactive with the reactants and the reaction products under the conditions of the reaction, a carboxylic acid, a steroid hydroxyl compound which has a cyclopentanophenanthrene carbon-carbon skeleton and contains up to a maximum of 40 carbon atoms and which is selected from the group consisting of steroid primary and secondary alcohols and phenols, and a carbodiimide, in the presence of a combination of a 4-(tertiary amino)-pyridine and a strong acid.

Primary, secondary, and phenolic hydroxyl group containing steroids suitable for esterification by carboxylic acids using the method of the present invention are steroids having a carbon-carbon skeleton selected from the group consisting of: estra-1,3,5(10)-triene, androstane, androst-4-ene, androst-5-ene, estr-4-ene, estr-5(10)-ene, pregn-4-ene, pregna4,6-diene, pregna-5-ene, pregna-1,4-diene, cholestane and cholest-5-ene.

It is preferred that the hydroxy group or groups which are to be esterified be located in the 3-, 16-, 17-, or 21-positions of said carbon-carbon skeletons.

Hydroxyl groups present in the steroids which are not to be esterified by the present method may be free, esterified with a monocarboxylic acid selected from the group consisting of lower alkanoic acids and benzoic acid, etherified with an alcohol selected from the group consisting of aliphatic and alicyclic alcohols having at most six carbon atoms, or transformed to an acetonide.

As examples of steroids and derivatives thereof which can be used as hydroxyl compounds in the present method, the following may be mentioned using the trivial names of the steroid as found in the literature (for example in the ninth edition of the Merck Index): Estrone; estradiol; estradiol 3-acetate; estradiol 17β-acetate; estriol; estriol 3-acetate; estriol 3,16α-diacetate; estriol 16α, 17β-diacetate; estradiol 3-methylether; estradiol 3-cyclopentylether; 17α-ethynylestradiol; androsterone; epiandrosterone; dihydrotestosterone; androstanediol; androstanediol 3α-acetate; testosterone; androstenediol; androstenediol 3β-acetate; dehydroepiandrosterone; 19-nortestosterone; ethynodiol; pregnenolone; deoxycorticosterone; cortisone; hydrocortisone; prednisone; prednisolone; prednisolone 17-benzoate; 9α-fluoro-16α-methylprednisolone; 9α-fluoro-16β-methylprednisolone; 9α-fluoro-16α-hydroxyprednisolone, 16,17-acetonide; and cholesterol.

Especially preferred steroids are estradiol, estriol, testosterone, dihydrotestosterone, 19-nortestosterone, deoxycorticosterone, cortisone, hydrocortisone, prednisone, and prednisolone.

Most preferred are 19-nortestosterone and prednisolone.

Carboxylic acids suitable to be transformed into their steroid carboxylic acid esters by the method of the present invention may have very different structures, but are in general expensive to buy or prepare. If such acids have substituents which may react with the carboxylic acid part of the molecule during the reaction conditions employed, e.g., reactive hydroxy-, amino- or thiol-groups, such groups may be protected by methods known per se during the reaction (see e.g. ref. (4) and (5)).

Preferred carboxylic acids are those with a molecular weight higher than 100.

Preferred carboxylic acids are alkanoic and alkenoic acids having 6 to 12 carbon atoms, and substituted or unsubstituted phenylalkanoic acids, having at most 22 carbon atoms and preferably having as one substituent in the benzene ring a bis β- or γ-haloalkyl substituted amino group or an alkoxy group having preferably three to twelve carbon atoms. Especially preferred acids of these types are: Heptanoic, decanoic, undecanoic, undecenoic and dodecanoic acids, 4-(bis(2-chloroethyl)aminophenyl)-2-aminopropionic acid, 3-(4-bis(2-chloroethyl)aminophenyl)-2-acetamidopropionic acid, 4-(4-bis(2-chloroethyl)aminophenyl)butyric acid and 3-(4-alkoxyphenyl)propionic acids such as 3-(4-propyloxyphenyl) propionic acid and 3-(4-hexyloxyphenyl)propionic acid.

Various types of carbodiimides may be employed, such as N,N$^1$-dicyclo-aliphatic, e.g., N,N$^1$-dicyclohexylcarbodiimide and N,N$^1$-dialiphatic, e.g., N,N$^1$-diisopropylcarbodiimide.

The preferred carbodiimide is N,N$^1$-dicyclohexylcarbodiimide.

The pyridine derivative used is a pyridine having a tertiary amine group, e.g., selected from the group consisting of di-lower-alkylamino, pyrrolidino, piperidino, morpholino, and 4-methylpiperidino in the 4-position. Other suitable tertiary amino groups are found in the literature, e.g., ref. (6) and (7).

It is preferably used in a catalytic amount in the range of 0.02 to 0.2 mole per mole of the limiting ester-forming component.

The strong acid may be an organic or an inorganic acid, such as a tri-halogene substituted acetic acid, e.g., trifluoroacetic acid or trichloroacetic acid, a sulfonic acid, e.g., p-toluenesulfonic acid or methanesulfonic acid, sulfuric acid, nitric acid, perchloric acid, or a hydrogen halide, e.g., hydrogen chloride, hydrogen bromide, or hydrogen iodide. It is preferred that such strong acids have a thermodynamic dissociation constant, expressed as their pK-values in water at 25° C., less than one. Examples of pK-values for some of these organic acids are as follows: trifluoroacetic acid and trichloroacetic acid both have pK-values of about 0.5, and p-toluenesulfonic acid and methanesulfonic acid have pK-values of about −1.3 and −1.5 respectively (8).

The sulfonic acids are preferred.

The strong acid is used in a catalytic amount, preferably in the range of 0.01 to 0.15 mole per mole of limiting ester-forming component. It is preferably used in a molar amount less than the molar amount of the 4-(tertiary amino)-pyridine employed. The preferred amount is in the range of 0.2 to 0.8 mole per mole of said 4-(tertiary amino)-pyridine.

The solvent employed may be any conventional solvent, well known in the art for esterification reactions, or a mixture of such solvents compatible with the reaction. Such solvent may be hydrocarbons, halogenated hydrocarbons, ethers, esters, ketones, or amides.

Among the halogenated and non-halogenated hydrocarbons the following may be mentioned as representative solvents: chloroform, methylene chloride, benzene, chlorobenzene, and toluene.

It is preferred that the ethers, esters, ketones, and amides are aliphatic. Representative examples of such solvents are dioxane, tetrahydrofurane, diethyl ether, ethyl acetate, acetone, butanone, and dimethyl formamide.

Methylene chloride and ethylacetate are the particularly preferred solvents.

Among the steroid esters prepared according to the present process the following may be especially mentioned:

21-(4-(4-N,N-bis(2-chloroethyl)amino)-phenyl)-butanoyloxy)-11,17-dihydroxy-pregna-1,4-diene-3,20-dione(=prednimustine);

17-(3-(4-hexyloxyphenyl)-propanoyloxy)estr-4-en-3-one(=Anadur ®) and 17-(decanoyloxy)-estr-4-en-3-one(=19-nortestosterone decanoate)

Reaction Temperature

The reaction may be conducted conveniently at room temperature. The reaction is frequently exothermic and can be controlled by a cooling process if desired.

The temperature is not critical except that it should not be so high as to produce undesirable side-effects, or so low that the reaction proceeds so slowly as to be at an uneconomic rate. The preferred range is 0°–30° C.

Reaction Pressure

The pressure used above the reaction mixture during the reaction is not particularly critical. For most purposes atmospheric pressure is adequate. In some cases, however, superatmospheric pressure may be desired and is serviceable. The pressure may also be below atmospheric pressure if desired.

Reaction Time

The reaction period may vary widely but for best yields and greatest economy the reaction must be allowed sufficient time to go to completion. Usually, at room temperature, less than ten hours reaction time is sufficient.

Molar Ratios

The ester-forming components, namely, the alcohol and the carboxylic acid, are generally employed in approximately equivalent amounts. However, excess of one reactant does not give rise to any detrimental effect upon the reaction except loss of economy and the usually attendant problems of incompletely reacted starting materials.

A slight molar excess of carbodiimide over the molar amount of the carboxylic groups is usually employed. Unreacted carbodiimide may subsequently be destroyed, if necessary, by the addition of a lower alkanoic acid, e.g., acetic acid.

Work-up Procedure

The reaction mixture containing the desired product is worked up according to normal procedures, as apparent to those skilled in the art.

In this disclosure the expression "lower" means that the group referred to contains one to four carbon atoms, inclusive. Thus, lower alkyl and lower alkanoic include: methyl, ethyl, propyl, isopropyl, butyl, isobutyl, secondary butyl, tertiary butyl, methanoic, ethanoic, propanoic. butanoic, and isobutanoic.

The nomenclature used in this disclosure is in accordance with the rules issued by the IUPAC Commission on the Nomenclature of Organic Chemistry, 1957, 1965, and 1971.

The following examples are intended to illustrate but not to limit the scope of the invention, although the reagents named and the esters obtained are of particular interest for our intended purposes.

EXAMPLE 1

Examples 3 and 5 in (1) were repeated using the same amounts of compounds as described in said examples, which are in accordance with the preparation of the same compounds as described by the inventors in their published paper (3).

After the addition of DCC both reaction mixtures start to become yellowish, and after a few hours at room temperature both reaction mixtures are strongly reddish-brown in colour.

After the recrystallization from isopropanol, prednimustine is obtained in 80% yield as cream-coloured crystals, having a m.p. of 164°–165° C. A further recrystallization from isopropanol using either activated carbon or silica gel as decolourizing agents gives in both experiments prednimustine with practically unchanged colour in about 85% yields.

When prednimustine is prepared according to Ex. 3, but the batchsize is increased about 100 times, the discolouration of the endproduct strongly increases, and its m.p. is found to be 162°–164° C. After several recrystallizations, using silica gel as a decolourizing agent, cream-coloured crystals are obtained with a m.p. of 164°–165° C.

The compound 17$\beta$-/3-(4-hexyloxyphenyl)-propanoyloxy)estr-4-en-3-one (Anadur ®) is obtained as a yellow-coloured product in 85% yield after recrystallization from methanol/water. The m.p. is 50°–52° C. Also in this case, further recrystallizations in the presence of activated carbon or silica gel do not remove the yellow colour.

Using $CH_2Cl_2$ or ethyl acetate as cosolvent and decreasing the amount of pyridine to the molar ratio of 0.3, calculated on 4-nortestosterone, results in that less than 50% of the steroid is esterified (according to TLC) even after a reaction time of 8 days.

Using the same experimental conditions as in Examples 3 and 5, but with pyridine replaced by the same amounts of 3- or 4-methylpyridine also give reddish-brown reaction mixtures and result in endproducts having the same colours as found with pyridine as solvent.

Using pyridine as solvent but replacing p-toluenesulfonic acid (in the following abbreviated as pTSA) by the corresponding molar amounts of perchloric acid, sulfuric acid, and hydrogen chloride do not change any of the discolourations.

When the amounts of pTSA in Example 3 and 5 are reduced 10 times, the colours of the reaction mixtures and the endproducts are still the same.

Finally, both examples are repeated without adding any pTSA at all. Now the reaction mixtures and the endproducts are not discoloured. On the other hand, both esters contain large amounts of impurities in the form of N-acylureas and of the respective carboxylic acid used in the experiment, resulting in decreased melting points and yields. Not even after several recrystallizations are these impurities removed.

EXAMPLE 2

Examples 1 and 2 in (1) were repeated with hexanol and phenol as hydroxy group containing reaction partners, resulting in colourless reaction mixtures and endproducts. The same results are obtained in these experiments, when the amounts of pTSA are increased according to (3).

EXAMPLE 3

The compounds obtained according to Example 8 in (1) are also prepared as described therein (the method of example 3). All the reaction mixtures but one have a reddish-brown colour after a few hours. The one which is not discoloured contains diethylstilbestrol and propionic acid. All the others result in strongly discoloured end products, having the expected melting points.

EXAMPLE 4

Anadur ® (see Ex. 1) is prepared according to the general procedure described in (2).

To a stirred solution of 5.48 g of 17 -hydroxyestr-4-en-3-one(19-nortestosterone, 20 mmol), 6 g 3-(4-hexyloxyphenyl)propionic acid (24 mmol), and 0.24 g 4-dimethylaminopyridine (DMAP, 2 mmol) in 50 ml $CH_2Cl_2$ is added at 0° C., 6.2 g of dicyclohexylcarbodiimide (DCC, 30 mmol). The reaction mixture is then stirred at room temperature for 3 hours. Precipitated urea is filtered off and the filtrate is treated as described in (2). After the final evaporation to dryness in vacuo the residue is crystallized from methanol/water. There is obtained 10.9 g of a compound (about 108% yield if calculated as Anadur ®) with no defined m.p. According to TLC the compound contains 19-nortestosterone and large amounts of N-acylurea formed with the acid and, even after several recrystallizations, it is still found to contain 0.53% N, corresponding to 8.6% of said N-acylurea.

Using the same molar ratio and reaction conditions, but starting with prednisolone and chlorambucil, gives similar results and no pure compounds are obtained after recrystallizations.

Also the 17-ester of 19-nortestosterone with decanoic acid is obtained as a crude product containing N-acylurea from the acid used and this impurity cannot be removed by recrystallizations.

EXAMPLE 5

To a stirred solution of 5.48 g 19-nortestosterone (20 mmol), 5.5 g 3-(4-hexyloxyphenyl)propionic acid (22 mmol), 0.24 g 4-dimethylaminopyridine (DMAP, 2 mmol) and 0.19 g p-toluenesulfonic acid (pTSA, 1 mmol) in 50 ml $CH_2Cl_2$ is slowly added at about 15° C. a solution of 5.2 g N,N'-dicyclohexylcarbodiimide (DCC, 25 mmol) in 30 ml $CH_2CL_2$. After 4 h at room temperature (no discolouration of the reaction mixture is seen) 1 ml of acetic acid is added to destroy the excess of DCC. Precipitated urea is then filtered off and the filtrate evaporated in vacuo. To the residue 50 ml ethyl acetate is added and, after stirring for 1 h, undissolved urea is filtered off and the filtrate evaporated in vacuo. The residue is crystallized from methanol/water. There is obtained 9.4 g of Anadur ® (93% yield) as white crystals having a m.p. of 53°-55° C. and being pure in TLC.

In a similar way pure, white crystals of Anadur ® is obtained from 19-nortestosterone (NT) and 3-(4-hexyloxyphenyl)propionic acid (PA) using the experimental conditions "No 1-27" as shown in Table 1 below, where the molar ratio NT:PA always is 1:1.1 and the others given are calculated on NT = 1,0. The reaction mixtures show no discolouration during the reaction times.

EXAMPLE 6

To a stirred solution of 5,48 g 19-nortestosterone, 4 g decanoic acid, 0.24 g DMAP and 0.19 g pTSA in 35 ml $CH_2Cl_2$ is slowly added at 10° C. a solution of 5.6 g DCC in 30 ml $CH_2Cl_2$. After 5 h at room temperature 2 ml acetic acid is added. The same work-up procedure as in Example 6 gives 7.6 g of pure 19-nortestosterone decanoate (88% yield) as white crystals from methanol/water. M.P. 35°-36° C.

In substantially the same manner the following 17-esters of 19-nortestosterone are prepared using the same molar ratio as above between steroid, acid, DMAP, pTSA and DCC.

The hexanoate, yield 85%, as a colourless oil. Pure according to TLS and NMR.

The chlorambucil ester, yield 91%, as a practically colourless oil. Pure according to TLC and NMR.

The hexahydrobenzoate, yield 80%, m.p. 89°-90° C. Pure in TLC.

The cinnamate, yield 95%, m.p. 183°-185° C. Pure in TLC.

EXAMPLE 7

To 250 ml $CH_2Cl_2$ is added with stirring 36 g prednisolone (0.10 mol), 31.3 g chlorambucil (0,103 mol), 1.2 g DMAP (0,01 mol) and 1.1 g pTSA (0,06 mol). The reaction mixture is cooled to 0° C. and with continued stirring at this temperature a solution of 22.7 g DCC (0,11 mol) in 50 ml $CH_2Cl_2$ is slowly added. The reaction mixture is then kept at 0° C. with stirring for 20 h. 3 ml acetic acid is added and precipitated urea filtered off. The filtrate is evaporated in vacuo and the residue recrystallized from ethanol to give 58.9 g of TLC pure prednimustine (91%) yield) without any discolouration. M.P. 165°-166° C.

The same results as above, including the yield, are obtained if $CH_2Cl_2$ is exchanged by ethyl acetate or DMAP is exchanged by the same molar amount of 4-morpholinopyridine.

In the above experiment chlorambucil is exchanged by 3-(phenyl)propionic acid (0,11 mol). After a reaction time of 6 h at 20° C., the 21-phenylpropionate of prednisolone is obtained in 90% yield. The compound is pure in TLC. M.p. 189°-191° C.

EXAMPLE 8

In a similar way as described in example 5, using the same reaction conditions, different steroids are esterified with 3-(phenyl)propionic acid resulting in the following esters (% yield and m.p. given below), which are all found to be pure in TLC and without any discolouration.

Estrone-3-phenylpropionate, 95%, 146°–147° C.
Estradiol-3-acetate-17-phenylpropionate, 96%, 125°–127° C.
Testosterone-17-phenylpropionate, 97%, 114°–115° C.
Dehydroepiandrosterone-3-phenylpropionate, 90%, 158°–159° C.
Androsterone-3-phenylpropionate, 86%, 160°–161° C.
Deoxycorticosterone-21-phenylpropionate, 89%, 138°–139° C.
Cortisone-21-phenylpropionate, 87%, 197°–6° C.
19-nortestosterone-17-phenylpropionate, 91%, 95°–96° C.
Cholesterol-3-phenylpropionate, 86%, 108°–110° C.
Hydrocortisone-21-phenylpropionate, 93%, 80°–81° C.

By exchanging the phenylpropionic acid above by benzoic acid, TLC pure Estrone-3-benzate, 91%, 217°–219° C. is obtained and by using 3-(4-propyloxyphenyl)propionic acid (2,2 mol as calculated on 1 mol estradiol), TLC pure Estradiol-3,17-bis-3-(4-propyloxyphenyl)-propionate, 89%, 72°–73° C. is prepared.

TABLE 1

(referring to example 5)

| No. | Molar ratio DCC | Molar ratio DMAP | Molar ratio pTSA | Reaction partner if not DCC, DMAP or pTSA | Reaction conditions Temp. °C. | Reaction conditions Time h | Solvent | Yield % |
|---|---|---|---|---|---|---|---|---|
| 1 | 1.25 | 0.1 | 0.05 | — | RT | 4 | CH$_2$Cl$_2$ | 93 |
| 2 | 1.5 | " | " | — | " | " | " | 96 |
| 3 | 1.25 | 0.2 | " | — | " | " | " | 92 |
| 4 | " | 0.01 | 0.005 | — | " | 8 | " | 91 |
| 5 | " | 0.1 | 0.1 | — | " | " | " | 85 |
| 6 | " | " | 0.2 | — | " | 24 | " | 75 |
| 7 | 1.25 | 0.1 | 0.05 | Di-isopropylcarbo-diimide | RT | 4 | CH$_2$Cl$_2$ | 91 |
| 8 | 1.25 | 0.1 | 0.05 | 4-diethylamino-pyridine | RT | 4 | CH$_2$Cl$_2$ | 94 |
| 9 | " | " | " | 4-piperidino-pyridine | " | " | " | 95 |
| 10 | " | " | " | 4-pyrrolidino-pyridine | " | " | " | 93 |
| 11 | " | " | " | 4-(4-methyl-1-piperidinyl)-pyridine | " | " | " | 94 |
| 12 | " | " | " | 4-morpholino-pyridine | " | 24 | " | 95 |
| 13 | 1.25 | 0.1 | 0.05 | CH$_3$SO$_3$H | RT | 4 | CH$_2$Cl$_2$ | 95 |
| 14 | " | " | " | H$_2$SO$_4$ | " | " | " | 93 |
| 15 | " | " | " | HCl | " | " | " | 96 |
| 16 | " | " | " | HNO$_3$ | " | " | " | 92 |
| 17 | " | " | " | HClO$_4$ | " | " | " | 93 |
| 18 | " | " | " | CF$_3$COOH | " | " | " | 95 |
| 19 | 1.25 | 0.1 | 0.05 | — | 0 | 20 | EtOAc | 93 |
| 20 | " | " | " | — | 10 | 7 | " | 92 |
| 21 | " | " | " | — | RT | " | Butanon | 94 |
| 22 | " | " | " | — | " | " | DMFA | 85 |
| 23 | " | " | " | — | " | 5 | CHCl$_3$ | 93 |
| 24 | " | " | " | — | " | 20 | Dioxane | 94 |
| 25 | " | " | " | — | " | " | THF | 95 |
| 26 | " | " | " | — | " | " | Acetone | 95 |
| 27 | " | " | " | — | " | 7 | Acetonitrile | 91 |

REFERENCES

1. The U.S. Pat. Ser. No. 4,180,504
2. Neises, B. and Steglich, W., Angew. Chem. Int. Ed. Engl. 17 (1978) 522
3. Holmberg, K. and Hansen, B., Acta Chem. Scand. B 33 (1979) 410
4. McOmic, J. F. W., Protective Groups in Organic Chemistry, Plenum Press London, 1973
5. Greene, T. W., Protective Groups in Organic Synthesis, John Wiley & Sons, New York, 1981
6. Hassner, A. et al, Tetraherdon 34 (1978) 2069
7. Goe, G. L. et al, Chemistry and Industry, 18 September, 1982, 722
8. Serjeant, E. P. and Dempsey, B., Ionisation Constants of Organic Acids in Aqueous Solution, Pergamon Press, 1979

We claim:

1. A process for the preparation of a steroid carboxylic acid ester of high purity and in improved yield and colour, comprising reacting in an inert organic solvent, which is nonreactive with the reactants and the reaction products under the condition of the reaction, a carboxylic acid, a steroid hydroxyl compound which has a cyclopentanophenanthrene carbon-carbon skeleton and contains up to a maximum of 40 carbon atoms, and which is selected from the group consisting of steroid primary or secondary alcohols and phenols, and a carbodiimide, in the presence of a combination of a 4-(tertiary amino)-pyridine and a strong acid.

2. A process of claim 1, wherein the 4-(tertiary amino)-pyridine is employed in a catalytic amount.

3. A process of claim 2, wherein the catalytic amount is in the range of 0.02 to 0.2 mole per mole of the limiting ester-forming component.

4. A process of claim 2, wherein the 4-(tertiary amino)-pyridine is selected from 4-dimethylaminopyridine, 4-pyrrolidinopyridine, 4-piperidinopyridine, 4-(4-methyl-1-piperidinyl)pyridine or 4-morpholinopyridine.

5. A process of claim 1, wherein the strong acid is employed in a catalytic amount.

6. A process of claim 5, wherein the catalytic amount is in the range of 0.01 to 0.15 mole per mole of the limiting ester-forming component.

7. A process of claim 5, wherein the strong acid is employed in an amount being less than the same molar amount of the 4-(tertiary amino)-pyridine employed.

8. A process of claim 7, wherein the strong acid is employed in an amount being 0.2 to 0.8 mole per mole of said 4-(tertiary amino)pyridine.

9. A process of claim 1, wherein the strong acid has an ionization constant, expressed as its pK-value in water at 25° C., lower than one.

10. A process of claim 9, wherein the strong acid is selected from the group consisting of sulfuric acid, nitric acid, perchloric acid, a hydrogen halide and a trihalogen substituted acetic acid.

11. A process of claim 10, wherein the strong acid in selected from the group consisting of trifluoroacetic acid and sulfonic acid.

12. A process of claim 11, wherein the sulfonic acid is selected from the group consisting of p-toluenesulfonic acid and methanesulfonic acid.

13. A process of claim 1, wherein the carbodiimide is present in a molar amount at least equivalent to the molar amount of carboxylic groups.

14. A process of claim 13, wherein the carbodiimide is selected from the group consisting of N,N'-dicyclohexylcarbodiimide and N,N'-diisopropyl-carbodiimide.

15. A process of claim 1, wherein the steroid hydroxyl compound is selected from estradiol, estriol, testosterone, dihydrotestosterone, 19-nortestosterone, deoxycorticosterone, cortisone, hydrocortisone, prednisone and prednisolone.

16. A process of claim 15, wherein the steroid hydroxyl compound is selected from the group consisting of 19-nortestosterone and prednisolone.

17. A process of claim 1, wherein the carboxylic acid has a molecular weight higher than 100.

18. A process of claim 8, wherein the carboxylic acid is selected from alkanoic or alkenoic acids having 6- to 12 carbon atoms such as heptanoic acid, decanoic acid, undecanoic acid, undecanoic acid and dodecanoic acid; or substituted or unsubstituted phenylalkanoic acids having at most 22 carbon atoms such as 4-(bis(2-chloroethyl)-aminophenyl)-2-aminopropionic acid; 3-(4-bis(2-chloroethyl)amino-phenyl)-2-acetamidopropionic acid, 4-(4-bis(2-chloroethyl)amino-phenyl)butyric acid and 3-(4-alkoxyphenyl)propionic acids.

19. A process of claim 1, wherein the reaction is performed in a solvent selected from hydrocarbons, halogenated hydrocarbons, ethers, esters, ketones or amides.

* * * * *

UNITED STATES PATENT AND TRADEMARK OFFICE
CERTIFICATE OF CORRECTION

PATENT NO. : 4,537,722

DATED : August 27, 1985

INVENTOR(S) : Anders R. Stamvik, Sten K. Kristensson and Karl-Erik Lundvall

It is certified that error appears in the above-identified patent and that said Letters Patent is hereby corrected as shown below:

Col. 12, line 20; "undecanoic" (second occurrence) should read -- undecenoic --

Signed and Sealed this

Eleventh Day of March 1986

[SEAL]

Attest:

DONALD J. QUIGG

Attesting Officer

Commissioner of Patents and Trademarks